United States Patent
Yonehara et al.

(10) Patent No.: US 8,008,085 B2
(45) Date of Patent: Aug. 30, 2011

(54) METHOD OF MEASURING HBA1C

(75) Inventors: Satoshi Yonehara, Kyoto (JP); Norio Inamura, Kyoto (JP)

(73) Assignee: ARKRAY, Inc., Kyoto (JP)

(*) Notice: Subject to any disclaimer, the term of this patent is extended or adjusted under 35 U.S.C. 154(b) by 182 days.

(21) Appl. No.: 12/377,232

(22) PCT Filed: Jan. 30, 2008

(86) PCT No.: PCT/JP2008/051390
§ 371 (c)(1),
(2), (4) Date: Feb. 11, 2009

(87) PCT Pub. No.: WO2008/093723
PCT Pub. Date: Aug. 7, 2008

(65) Prior Publication Data
US 2010/0178659 A1 Jul. 15, 2010

(30) Foreign Application Priority Data

Jan. 30, 2007 (JP) .................................. 2007-020185

(51) Int. Cl.
*G01N 33/72* (2006.01)
*G01N 33/48* (2006.01)

(52) U.S. Cl. .............. 436/67; 436/63; 436/66; 436/124; 436/164; 436/166; 436/174; 435/23; 435/28

(58) Field of Classification Search .............. 436/8, 15, 436/63, 66, 67, 79, 110, 119, 124, 164, 166, 436/174; 422/61, 430; 435/23, 28, 29; 252/408.1
See application file for complete search history.

(56) References Cited

U.S. PATENT DOCUMENTS

| | | | |
|---|---|---|---|
| 3,859,049 A * | 1/1975 | Ware et al. ............ | 436/11 |
| 5,712,138 A | 1/1998 | Kato et al. | |
| 5,789,221 A | 8/1998 | Kato et al. | |
| 5,824,527 A | 10/1998 | Kato et al. | |
| 6,033,867 A | 3/2000 | Kato et al. | |
| 6,797,503 B1 | 9/2004 | Ishimaru et al. | |
| 6,825,016 B1 | 11/2004 | Ishimaru et al. | |
| 7,235,378 B2 | 6/2007 | Yonehara | |
| 2003/0162242 A1 * | 8/2003 | Yonehara .................. | 435/25 |
| 2005/0176086 A1 | 8/2005 | Yonehara et al. | |
| 2006/0172367 A1 | 8/2006 | Yoshida et al. | |
| 2007/0031910 A1 | 2/2007 | Hirai et al. | |

FOREIGN PATENT DOCUMENTS

| | | |
|---|---|---|
| JP | 7-289253 | 11/1995 |
| JP | 8-154672 | 6/1996 |
| JP | 8-336386 | 12/1996 |
| JP | 2000-065839 | 3/2000 |
| JP | 2000-300294 | 10/2000 |
| JP | 2002-082105 | 3/2002 |
| JP | 2002-315600 | 10/2002 |
| JP | 2003-207497 | 7/2003 |
| JP | 2004-275013 | 10/2004 |
| JP | 2004-275063 | 10/2004 |
| JP | 2004-344052 | 12/2004 |
| WO | 97/20039 | 6/1997 |
| WO | 00/50579 | 8/2000 |
| WO | 00/61732 | 10/2000 |
| WO | 02/06519 | 1/2002 |
| WO | 03/097865 | 11/2003 |
| WO | 2004/029251 | 4/2004 |
| WO | 2004/106919 | 12/2004 |

OTHER PUBLICATIONS

Yonehara et al., "Enzymatic assay of Glycohemoglobin", Bioscience and Industry, vol. 62, No. 3, pp. 181-182, 2004 with partial translation.
Raabo, et al., "External Quality Assessment in Primary Health Care by Using Fresh Whole Blood", Clinical Chemistry, vol. 40, No. 12, pp. 2223-2226, 1994.
Honda et al., "Changes in 2,3-DPG Content and Oxygen Affinity in Erythrocytes Stored at 4° C.", Vox Sanguinis, vol. 37, No. 4, pp. 229-234, 1979.
Jury et al., "Clinical Importance of the Reversible Fraction of Haemoglobin $A_{1c}$ in Type 2 (Non-Insulin-Dependent) Diabetes", Diabetologia, vol. 25, pp. 313-315, 1983.
Wang, "Analysis of antiglycolytic activity of the glyceraldehyde in whole blood specimens," J. of Chinese Microcirculation, 8(5): 313-316 (2004).
Office Action issued in Chinese Application No. 200880003239.7 dated May 25, 2011.

* cited by examiner

*Primary Examiner* — Maureen M Wallenhorst
(74) *Attorney, Agent, or Firm* — Morgan, Lewis & Bockius LLP

(57) ABSTRACT

A method of measuring HbA1c is provided that, even with a whole blood sample after storage, measurement accuracy substantially equal to a whole blood sample right after collection can be maintained. Whole blood is stored in a presence of a glycolytic inhibitor and protease is added to the stored whole blood sample to cleave hemoglobin in the whole blood sample. Then a glycated part of a hemoglobin fragment thereby obtained is treated with fructosyl amine oxidase. Thereafter, a glycation degree of HbA1c is determined by measuring a redox reaction between the glycated part and the fructosyl amine oxidase. Further, instead of storage of the whole blood in a presence of the glycolytic inhibitor, a strong electrolyte substance such as KCl, $K_2SO_4$, KNO, NaCl, $Na_2SO_4$, NaNO, $MgCl_2$, $MgSO_4$, $Mg(NO)_2$, etc. is added to the whole blood after storage and a protease treatment is performed in a presence of the strong electrolyte substance. According to these methods, fluctuation in a measurement value of HbA1c due to storage of the whole blood can be avoided.

12 Claims, No Drawings

METHOD OF MEASURING HBA1C

TECHNICAL FIELD

The present invention relates to a method of producing a hemoglobin-containing sample used for a measurement of HbA1c and a method of measuring HbA1c.

BACKGROUND ART

As an indicator for showing a biological state, the glycation degrees of various kinds of proteins are measured. Among them, a glycation degree of hemoglobin (Hb) in a blood cell, in particular, HbA1c is used as an important indicator in diagnoses, treatments and the like for diabetes, because the HbA1c reflects histories of an in-vivo blood glucose level. The HbA1c has a structure in which a glucose is bonded to a β chain N-terminal amino acid (valine) of HbA ($\alpha_2\beta_2$), and its value is represented by a ratio (proportion or %) of a HbA1c amount with respect to a total Hb amount.

HbA1c is measured, for example, by a high-performance liquid chromatography (HPLC) method, an immunization method, an enzymatic method, and an electrophoresis method. Recently, the establishment of an easy-to-use measurement by the enzymatic method has been studied. An example of the method of measuring HbA1c by the enzymatic method is as follows. First, Hb is treated with protease and a fragment containing a β chain N-terminal valine is cleaved. Then, fructosyl amine oxidase (hereinafter, referred to as "FAOD") is allowed to act on a glycated part of the fragment (i.e., a glycated part of the β chain N-terminal valine), thereby generating hydrogen peroxide. The amount of this hydrogen peroxide corresponds to a glycation amount of the β chain N-terminal valine of the Hb. Then, peroxidase (hereinafter, referred to as "POD") and a chromogenic substrate that develops color by oxidation are added further to this reaction solution, so that a redox reaction occurs between the hydrogen peroxide and the chromogenic substrate with the POD as a catalyst. Thereafter, a chromogenic level of the chromogenic substrate is measured, for example, by an absorbance measurement. In this method, the level of the absorbance corresponds to an amount of colored chromogenic substrate, the amount of the colored chromogenic substrate corresponds to an amount of generated hydrogen peroxide, and the amount of the hydrogen peroxide corresponds to the amount of glycation as described above. In other words, the glycation amount can be measured indirectly by measuring the chromogenic level of the chromogenic substrate through such redox reaction. Further, HbA1c (%) can be calculated from this glycation amount and a total Hb amount.

This kind of measurement of HbA1c (%) often is performed by an inspection agency. Particularly in a case of medical examination, etc., normally, Hb-containing samples (for example, a whole blood sample, a blood cell sample collected from whole blood, a Hb sample collected from the whole blood) collected from patients are not subjected to a measurement right after collection. In general, these Hb-containing samples are subjected to the measurement after storage at room temperature, or in a refrigerated or frozen condition.

DISCLOSURE OF THE INVENTION

However, when the inventors of the present invention have carried on a study on the aforementioned enzymatic method, the following has been discovered. That is, it is found that when the measurement of HbA1c is performed on the aforementioned Hb-containing sample after storage, the measurement value thereof is lower than that of the Hb-containing sample right after collection. Therefore, with respect to the Hb-containing sample to be measured after storage, there is a problem that it is difficult to maintain a measurement accuracy substantially equal to the Hb-containing sample right after collection. Particularly, because HbA1c reflects the past history of the in-vivo blood glucose level as described above, it is very important to know a change in the measurement value over time rather than a single measurement value in treatment and prevention for diabetes. Therefore, with respect to factors that vary the measurement value, it is desirable to standardize conditions. However, also from an aspect of efficiency, it is not realistic to keep conditions (e.g., time, temperature, etc.) from the collection to the measurement of the Hb-containing sample constant.

Hence, an object of the present invention is to provide a method of measuring HbA1c that maintains a measurement accuracy substantially equal to the Hb-containing sample right after collection even with the Hb-containing sample after storage.

A method of producing a Hb-containing sample of the present invention is a method of producing a Hb-containing sample used for a method of measuring HbA1c, wherein the method includes:

(A1) a process of storing a Hb-containing material in a state in which carbon dioxide generation is inhibited; or (A2) a process of reducing carbon dioxide bonded to Hb in a Hb-containing material after storage.

A method of measuring HbA1c of the present invention is a method of measuring HbA1c, wherein the method includes:

(A) a process of preparing a Hb-containing sample after storage by a method of producing according to the present invention;

(B) a process of cleaving hemoglobin in the Hb-containing sample by applying a protease treatment to the Hb-containing sample after storage;

(C) a process of treating a glycated part of a hemoglobin fragment obtained by the process (B) with fructosyl amine oxidase; and (D) a process of determining a HbA1c amount by measuring a redox reaction between the glycated part and the fructosyl amine oxidase.

The inventors of the present invention have been conducting a study on causes of variation in HbA1c due to storage of the Hb-containing sample. As a result, they found out that the causes thereof are generation of carbon dioxide because of storage of the Hb-containing sample and a structural change of Hb due to the generated carbon dioxide. Generally, even with a sample collected from a body, for example, when the sample contains a blood cell, because the blood cell itself is alive, it is known that glucose is consumed and thereby carbon dioxide is generated by a glycolytic system. An oxygen pressure in whole blood of a healthy subject right after collection is, normally, about 80 to 100 mmHg and a carbon dioxide pressure in the whole blood of the healthy subject right after collection is, normally, about 35 to 45 mmHg. Further, it is known that carbon dioxide is present as carbonate ion ($HCO^{3-}$) in whole blood and a concentration of the carbonate ion is about 22 to 26 mmol (for example, 24 mmol). However, for example, when the whole blood is left at room temperature for 1 to 5 days, due to the glycolytic system, the oxygen pressure is reduced to about 0 mmHg, the carbon dioxide pressure becomes at least 150 mmHg, and the concentration of the carbonate ion is increased to about 8 to 34 mmol. This carbonate ion concentration is almost twice as high as a concentration of the glucose in the whole blood right after collection. In other words, because of storage, a ratio of an oxygen concentration and a carbon dioxide concentration in the whole blood is reversed. In this manner, when a ratio of carbon dioxide is increased, the steric structure of Hb is converted from an oxy form to a deoxy form. Such conversion to the deoxy form is not limited to the whole blood and, for example, also occurs in a blood cell sample collected from the whole blood and a Hb sample collected from the whole blood because of storage in a presence of carbon dioxide or storage in a state in which carbon dioxide is generated. Further, as a result of a further study, it is found that deoxy form Hb has a steric structure in which a β chain N-terminal faces inward. The β chain N-terminal is very important to the measurement of HbA1c by the enzymatic method. In other words, with a conventional method, due to generation of carbon dioxide during storage, the steric structure of Hb is converted to the deoxy form in which the β chain N-terminal is hardly treated with protease, and it is difficult to maintain all the Hb in the oxy form. Therefore, the measurement value of HbA1c may be lowered as a result of storage. The deoxy form Hb has a structure in which the β chain N-terminal is faced inward and therefore the β chain N-terminal valine and peptide containing the β chain N-terminal valine are hardly cleaved by the protease. This fact was discovered by the inventors of the present invention for the first time, although there is a report about the oxy form and the deoxy form as the steric structure of Hb. As a first method, by inhibiting the generation of carbon dioxide during storage of the Hb-containing material, the inventors of the present invention realized a prevention of fluctuation in HbA1c due to storage. Further, as a second method, even when Hb is converted to the deoxy form because of generation of carbon dioxide in the Hb-containing material due to storage, by reducing carbon dioxide bonded to Hb and reconverting Hb to the oxy form, the inventors of the present invention realized a prevention of fluctuation in HbA1c due to storage.

As described above, according to the present invention, even when the Hb-containing material is stored, because fluctuation in the measurement value of HbA1c can be prevented, the HbA1c of the Hb-containing sample after storage can be measured with substantially equal accuracy to that of the Hb-containing sample right after collection. Accordingly, since an effect on the measurement value of HbA1c due to storage can be prevented, as described above, it may be said that the method of the present invention is very useful in a case in which the sample is required to be stored, namely when the measurement of HbA1c is performed at a place different from a sampling point, when the measurement of HbA1c is performed after collecting a certain number of samples, etc. However, the aforementioned mechanism is mere supposition and does not limit the present invention at all.

BEST MODE FOR CARRYING OUT THE INVENTION

<Method of Producing Hb-Containing Sample>

A method of producing of the present invention is, as described above, a method of producing a Hb-containing sample used for a method of measuring HbA1c, wherein the method includes:
(A1) a process of storing a Hb-containing material in a state in which carbon dioxide generation is inhibited; or
(A2) a process of reducing carbon dioxide bonded to Hb in a Hb-containing material after storage.

As described above, (A1) by storing the Hb-containing material in a state in which carbon dioxide generation is inhibited or (A2) by reducing carbon dioxide bonded to Hb in the Hb-containing material after storage, the Hb-containing sample in which fluctuation in a measurement value of HbA1c is prevented can be obtained. In the present invention, as long as the carbon dioxide generation is inhibited during storage or the carbon dioxide that is generated during storage and bonded to Hb is reduced, a method of inhibiting carbon dioxide generation or a method of reducing the generated carbon dioxide is not limited at all. With the Hb-containing sample after storage prepared in the aforementioned manner, in the measurement of HbA1c, for example, HbA1c can be measured with substantially equal accuracy to that of the Hb-containing sample right after collection. The method of measuring HbA1c using the Hb-containing sample produced according to the present invention is not limited at all. Specifically, for example, besides the enzyme method as described later, conventionally known methods such as an immunization method, an HPLC method, etc. are applicable. The method of producing the Hb-containing sample of the present invention is explained in detail in the method of measuring HbA1c of the present invention.

In the present invention, the Hb-containing material to be stored is applicable as long as it contains Hb. Examples of the Hb-containing material include whole blood, blood cell, etc. Examples of the whole blood include untreated whole blood after collection (blood collection), diluted whole blood, hemolyzed whole blood, etc. Further, examples of the blood cell include blood cell collected from the whole blood, diluted blood cell, hemolyzed blood cell, etc. The blood cell can be collected from the whole blood, for example, by sedimentation, centrifugation, etc. In this state, plasma or the like may be remained. Further, the Hb-containing material can be Hb (for example, purified Hb) collected from the whole blood after blood collection. Preferably, the process (A1) is applied to storage of the Hb-containing material that contains blood cell such as untreated whole blood, diluted whole blood, blood cell, etc. Preferably, the process (A2) is applied to storage of the Hb-containing material such as untreated whole blood, diluted whole blood, hemolyzed whole blood, blood cell, purified Hb, etc. In this state, the Hb-containing material may be dry (dry material) or wet (liquid).

<Method of Measuring HbA1c>

A method of measuring HbA1c of the present invention is a method of measuring HbA1c, wherein the method includes:
(A) a process of preparing a Hb-containing sample after storage by a method of producing according to the present invention;
(B) a process of cleaving hemoglobin in the Hb-containing sample by applying a protease treatment to the whole blood sample after storage;
(C) a process of treating a glycated part of a hemoglobin fragment obtained by the process (B) with fructosyl amine oxidase; and
(D) a process of determining a HbA1c amount by measuring a redox reaction between the glycated part and the fructosyl amine oxidase.

With respect to the method of measuring of the present invention, in the process (A), as described above, the Hb-containing sample after storage may be prepared by (A1) storing the Hb-containing material in a state in which carbon dioxide generation is inhibited or (A2) reducing carbon dioxide bonded to Hb in the Hb-containing material after storage. Hereinafter, a first method of measuring HbA1c as a specific example of the former and a second method of measuring HbA1c as a specific example of the latter are described. However, the present invention is not limited to those specific examples.

First Method of Measuring HbA1c

A first method of measuring HbA1c of the present invention includes:

(A1') a process of storing a Hb-containing material in a presence of a glycolytic inhibitor (producing a Hb-containing sample after storage);

(B) a process of cleaving hemoglobin in the Hb-containing sample by applying a protease treatment to the Hb-containing sample after storage;

(C) a process of treating a glycated part of a hemoglobin fragment obtained by the process (B) with fructosyl amine oxidase; and (D) a process of determining a HbA1c amount by measuring a redox reaction between the glycated part and the fructosyl amine oxidase.

According to the first method of measuring HbA1c, for example, in a case of the Hb-containing material that contains blood cell, because a glycolytic system of the blood cell is controlled during its storage, carbon dioxide generation is inhibited. As a result, conversion of the steric structure to a deoxy form Hb is prevented. Therefore, even with the Hb-containing sample after storage, the steric structure of Hb can maintain an oxy form in which the protease is easily act on a β chain N-terminal, the same as at the time of blood collection, and therefore fluctuation in the measurement value of HbA1c can be prevented. The process (A1') preferably is applied to storage of the Hb-containing material that contains blood cell such as untreated whole blood, diluted whole blood, blood cell, etc.

With respect to the first method of measuring HbA1c, for example, as long as the Hb-containing material is stored in the presence of the glycolytic inhibitor in the process (A1'), conditions in other processes are not limited at all. The processes (B) and (C) may be performed simultaneously in the same reaction solution. Further, the process (D) may be performed after the process (C) or may be performed at the same time with the process (C) (and process (B)).

Examples of the glycolytic inhibitor include sodium fluoride, potassium fluoride, etc. Among them, sodium fluoride is preferable. Further, the glycolytic inhibitor may be used alone or two or more of them may be used in combination.

Next, the first method of measuring HbA1c of the present invention is explained with an example in which the whole blood is stored as the Hb-containing material. However, the present invention is not limited thereto and may be applied in the same manner with respect to the Hb-containing material such as diluted whole blood, blood cell, etc.

(Storage of Whole Blood)

Whole blood is collected from a test body and stored in the presence of the glycolytic inhibitor until the measurement of HbA1c. Although storage of the whole blood may not be necessary in the measurement of HbA1c, because an object of the present invention is to prevent fluctuation in a HbA1c value due to storage, the present invention is preferably applied in a case where storage of the whole blood is required.

The glycolytic inhibitor may be added right after collection of the whole blood from the test body or preliminarily may be placed in a blood collecting device (e.g., blood collecting tube). Specific examples of the blood collecting tube containing sodium fluoride include commercial products such as VENOJECT II vacuum blood collecting tube (trade name) manufactured by Terumo, Glucosave (trade name) manufactured by SEKISUI, etc. Further, when a commercially available blood collecting tube is used, for example, an anticoagulant such as heparin may further be contained. By coexisting the anticoagulant such as heparin, a sufficient anticoagulant effect can be ensured. In the present invention, a reagent containing the glycolytic inhibitor may be used as a storage reagent of the whole blood.

In the process (A1'), a ratio of the glycolytic inhibitor to be added relative to the whole blood is not particularly limited, however is, for example, 0.1 to 100 mol/L and preferably 0.2 to 10 mol/L per ml of the whole blood. In a reaction solution for the protease treatment in the process (B), a concentration of the glycolytic inhibitor (e.g., NaF) is, for example, 0.01 to 10 mol/L and preferably 0.01 to 3 mol/L.

The whole blood to which the glycolytic inhibitor is added can be stored about 10 days from a day of the blood collection, although it is not particularly limited. For example, in a case where the whole blood is forwarded to an inspection agency, the whole blood collected from patients is generally subjected to an analysis within 2 days from the day of the blood collection. Further, according to the conventional method, for example, an effect on the measurement value of HbA1c becomes obvious after 4 days from the day of the blood collection. Therefore, according to the present invention, even when a blood collection sample is stored, variation in HbA1c % can be prevented sufficiently and a reliable measurement of HbA1c can be performed.

A storage temperature of the whole blood to which the glycolytic inhibitor is added is not particularly limited. Generally, the storage temperature is 1 to 35° C., preferably 2 to 25° C., and more preferably 2 to 10° C.

Besides the aforementioned untreated whole blood, for example, diluted whole blood and collected blood cell can be stored in the same manner as described above. A ratio of the glycolytic inhibitor to be added is not particularly limited. For example, the ratio can be set in the aforementioned range by converting the diluted whole blood and the blood cell into a whole blood amount. The same applies to the following processes.

(Hemolysis Treatment)

The whole blood sample after storage is subjected to a hemolysis treatment. A method of hemolyzing the whole blood sample is not particularly limited. Examples of the method include a method using an osmotic pressure difference, a method using ultrasonic wave, etc. In a case of the method using the osmotic pressure difference, the whole blood (or blood cell) may be hemolyzed, for example, by adding purified water that is 2 to 100 times as much as the whole blood (or blood cell) in volume. Further, the sample may be hemolyzed by adding a surfactant.

(Protease Treatment)

The hemolyzed whole blood sample after storage is subjected to the protease treatment. In this treatment, a β chain N-terminal valine of Hb of the sample and a peptide containing the N-terminal valine (β chain N-terminal peptide) are cleaved so that the later described FAOD can act efficiently on the glycated part of Hb (β chain N-terminal valine).

Examples of the protease include metalloprotease, serine protease, serine carboxypeptidase, proteinase K, bromelain, papain, trypsin derived from porcine pancreas, protease derived from *Bacillus subtilis*, protease derived from *Aspergillus oryzae* and the like, and endoprotease is preferably used. Commercially available products that can be used for the protease include, for example, metalloprotease (trade name) manufactured by Arkray, Inc., protease A "Amano" G (trade name) manufactured by Amano Enzyme Inc., protease M "Amano" G (trade name) manufactured by Amano Enzyme Inc., protease S "Amano" G (trade name) manufactured by Amano Enzyme Inc., peptidase R (trade name) manufactured by Amano Enzyme Inc., papain M-40 (trade name) manufactured by Amano Enzyme Inc., protease N (trade name) manufactured by Fluka Chemie AG, protease N "Amano" (trade name) manufactured by Amano Enzyme Inc., metalloproteinase derived from the genus *Bacillus* manufactured by Toyobo Co., Ltd. under the trade name of Toyoteam, etc.

Particularly, protease that acts specifically on the β-chain N-terminal and catalyzes the cleavage of the N-terminal peptide (for example, JP 2000-300294 A and JP 2004-344052 A) preferably is used. Further, examples of the protease that catalyzes the cleavage of the β chain N-terminal valine include proteases disclosed in WO 2000/50579 A1 (Japanese Patent No. 3668801), WO 2000/61732 A1, JP 2002-315600 A and the like.

A ratio of the protease to be added in this reaction solution is, for example, in the range of 0.001 to 300,000 KU/L, preferably in the range of 0.01 to 30,000 KU/L, and particularly preferably in the range of 0.1 to 1000 KU/L. In a case where a concentration of Hb in the aforementioned reaction solution is 0.005 mM, a ratio of the protease to be added is, for example, in the range of 0.01 to 300,000 KU/L, preferably in the range of 0.05 to 30,000 KU/L, and particularly preferably in the range of 0.1 to 10,000 KU/L. With respect to protease activity "U", the amount of enzyme that increases the absorbance of 275 nm per minute which is equivalent to one micromole of tyrosine is defined as 1U.

The protease treatment preferably is performed, for example, in a buffer solution. As the buffer solution, a Tris-HCL buffer solution, an EPPS buffer solution, a PIPES buffer solution, a phosphoric acid buffer solution, an ADA buffer solution, a citric acid buffer solution, an acetic acid buffer solution, and the like can be used. Further, pH of a protease reaction solution is, for example, in the range of 4 to 10 and preferably in the range of 6 to 9.

Conditions of the protease treatment are not particularly limited. A treatment temperature is, for example, in the range of 10 to 40° C. and preferably in the range of 25 to 37° C. A treatment time is, for example, about 1 to 100 minutes and preferably 1 to 10 minutes.

Further, this protease treatment may be performed in the presence of the later described accelerating compound. When Hb is applied with the protease treatment in the presence of such accelerating compound, the protease treatment can be more efficient and less time-consuming. Further, because an efficient protease treatment can be performed, for example, an increase of protease used for the treatment becomes unnecessary.

An example of the accelerating compound includes a compound represented by the following Formula (I).

$$R—X \tag{I}$$

In the Formula (I), R represents an alkyl group, a substituted alkyl group, an acyl group, or a substituted acyl group with a carbon number of 9 or more. Specific examples include a straight-chain alkyl group or a straight-chain acyl group with a carbon number of 9 to 16, a branched-chain alkyl group or a branched-chain acyl group with a carbon number of 10 to 40 and a main-chain carbon number of 9 to 16, a straight-chain alkyl group that is substituted by cycloalkyl (for example, a carbon number of the cycloalkyl ranges from 3 to 8, and a carbon number of the straight chain except for the cycloalkyl ranges from 4 to 13) and the like. Examples of the cycloalkyl include cyclohexyl, cyclopenthyl, cyclobutyl and the like. In the above Formula (I), X represents a sugar residue, and preferably is a residue of a monosaccharide or a disaccharide, for example. Examples of the monosaccharide include mannoside, glucoside, thioglucoside and the like, and examples of the disaccharide include maltoside, fructopyranosyl-glucopyranoside, thiomaltoside and the like. Structures of these sugars may be any of α, β, D or L. Moreover, hydrogen to be bonded to a cyclic structure of the sugar and hydrogen in an OH group may be substituted by Na, K, halogen or the like, for example. Incidentally, in the present invention, atoms via which R and the cyclic structure of the sugar residue are bonded (for example, —O—, —S— and the like) are components of the sugar residue.

Examples of the accelerating compound of the Formula (I) include n-dodecyl-β-D-maltoside (n-dodecyl-β-D-maltopyranoside), 6-cyclohexylhexyl-β-D-maltoside, sucrose monolaurate (β-D-fructopyranosyl-α-D-glucopyranoside monododecanoate), n-decyl-β-D-maltoside (n-decyl-β-D-maltopyranoside), n-nonyl-β-D-thiomaltoside (n-nonyl-β-D-thiomaltoside), 5-cyclohexylpenthyl-β-D-maltoside, undecyl-β-D-maltoside, n-dodecyl-αβ-D-maltoside, hexadecyl-β-D-maltoside and 3-oxatridecyl-α-D-mannoside and the like. Among them, n-dodecyl-β-D-maltoside, sucrose monolaurate, hexadecyl-β-D-maltoside and the like, whose carbon number of R (alkyl chain) in the above Formula (I) are 12 or more, are preferable. Moreover, in a case where the carbon numbers of R are the same (for example, the alkyl group and the acyl group that are the same in carbon number), the acyl group is more preferable, so that n-dodecyl-β-maltoside (n-dodecyl-β-D-maltopyranoside) is preferable.

A ratio of the accelerating compound to be added in the reaction solution for the protease treatment is, for example, in the range of 0.01 to 200 mM and preferably in the range of 0.4 to 100 mM. When the concentration of Hb in the reaction solution is 0.005 mM, a ratio of the accelerating compound to be added is, for example, in the range of 0.4 to 100 mM and preferably in the range of 1 to 100 mM. In this state, the addition order of the accelerating compound and the protease is not limited at all. They can be added simultaneously or in random order.

Conditions of the protease treatment are not particularly limited as described above, and in a case where the accelerating compound is present, a treatment time thereof is not limited. Particularly, the upper limit of the treatment time is not limited and, for example, the protease treatment can be performed about 0.1 to 60 minutes. The treatment time is preferably 0.1 to 45 minutes, more preferably 0.2 to 20 minutes, and particularly preferably 0.2 to 5 minutes. When the protease treatment is performed in the presence of the accelerating compound, amino acid and peptide can be cleaved promptly, and therefore a sufficient cleavage treatment can be performed within the aforementioned treatment time.

Besides the compound represented by the Formula (I), an example of the accelerating compound includes a nitro compound. The nitro compound may be used alone or two or more of them may be used in combination. Examples of this nitro compound include nitrous acid and its salt. The nitrous acid is not particularly limited, and may be, for example, potassium nitrite, amyl nitrite, butyl nitrite, nitroglycerin, sodium nitrite, paranitrochlorbenzene, trinitrotoluene, nitrobenzene and the like. A ratio of the nitro compound to be added in the reaction solution for the protease treatment is not particularly limited. For example, in a case where the concentration of Hb in the reaction solution is 0.005 mM, the ratio of the nitro compound to be added is, for example, preferably 0.005 mM or more, and more preferably 0.05 to 2 mM.

Further, in advance of a FAOD treatment which is the next process, a tetrazolium compound preferably is added to the sample. In a case of the sample containing a reducing substance such as ascorbic acid like a blood sample, for example, an effect on a measurement because of it can be avoided by adding the tetrazolium compound. In this case, an addition of the tetrazolium compound may be performed before or after the protease treatment. Further, at the time of the protease treatment, when the tetrazolium compound is present, for example, digestion by the protease can be promoted. The tetrazolium compound is not particularly limited and includes, for example, 2-(4-iodophenyl)-3-(4-nitrophenyl)-5-(2,4-disulfophenyl)-2H-tetrazolium salt, 2-(4-iodophenyl)-3-(2,4-dinitrophenyl)-5-(2,4-disulfophenyl-2H-tetrazolium salt, 2-(2-methoxy-4-nitrophenyl)-3-(4-nitrophenyl)-5-(2,4-disulfophenyl-2H-tetrazolium salt, 2-(4-iodophenyl)-3-(4-nitrophenyl)-5-phenyl-2H-tetrazolium salt, 3,3'-(1,1'-biphenyl-4,4'-diyl)-bis(2,5-diphenyl)-2H-tetrazolium salt, 3,3'-[3,3'-dimethoxy-(1,1'-biphenyl)-4,4'-diyl]-bis[2-(4-nitropenyl)-5-phenyl-2H-tetrazolium salt], 2,3-diphenyl-5-(4-chlorophenyl)tetrazolium salt, 2,5-diphenyl-3-(p-diphenyl)tetrazolium salt, 2,3-diphenyl-5-(p-diphenyl)tetrazolium salt, 2,5-diphenyl-3-(4-styrylphenyl)tetrazolium salt, 2,5-diphenyl-3-(m-tolyl)tetrazolium salt, 2,5-diphenyl-3-(p-tolyl)tetrazolium salt, 2,3-diphenyl-5-(2-thienyl)tetrazolium salt, 2-benzothiazoyl-3-(4-carboxy-2-methoxyphenyl)-5-[4-(2-sulfoethylcarbamoyl)phenyl]-2H-tetrazolium salt, 2,2'-dibenzothiazolyl-5,5'-bis[4-di(2-sulfoethyl)carbamoylphenyl]-3,3'-(3,3'-dim ethoxy-4,4'-biphenylene)ditetrazolium salt, 3-(4,5-dimethyl-2-thiazoyl-2,5-diphenyl-2H-tetrazolium salt, 2,3-diphenyl-5-cyanotetrazolium salt, 2,3-diphenyl-5-carboxytetrazolium salt, 2,3-diphenyl-5-methyltetrazolium salt, 2,3-diphenyl-5-ethyltetrazolium salt, etc. Among them, 2-(4-iodophenyl)-3-(2,4-dinitrophenyl)-5-(2,4-disulfophenyl)-2H-tetrazolium salt is preferable.

A ratio of the tetrazolium compound to be added is not particularly limited. For example, the ratio of the tetrazolium compound is preferably 0.001 to 100 μmol per μL of the sample, more preferably in the range of 0.005 to 10 μmol, and particularly preferably in the range of 0.01 to 1 μmol.

(FAOD Treatment)

Next, FAOD is added to a reaction solution after the protease treatment. Thereby, the FAOD acts on the glycated part of the N-terminal valine of a Hb fragment to cause a redox reaction. Due to this FAOD treatment, for example, as described later, sugar bonded to the N-terminal valine is released and thereby hydrogen peroxide is generated.

FAOD is not particularly limited however is preferably an enzyme that catalyzes a reaction in which an α-amino group acts on the glycated amino acid or the glycated peptide so as to generate hydrogen peroxide and α-keto aldehyde (hereinafter, referred to as "FAOD-α"). Such catalytic reaction can be represented by the following Formula (1)

$$R^1-CO-CH_2-NH-R^2+H_2O+O_2 \rightarrow R^1-CO-CHO+NH_2-R^2+H_2O_2 \quad (1)$$

In Formula (1) above, $R^1$ represents a hydroxyl group or a residue derived from a sugar before a glycation reaction (i.e., sugar residue). The sugar residue ($R^1$) is an aldose residue when the sugar before the reaction is an aldose, and it is a ketose residue when the sugar before the reaction is ketose. For example, when the sugar before the reaction is a glucose, it takes a fructose structure after the reaction by an Amadori rearrangement. In this case, the sugar residue ($R^1$) becomes a glucose residue (aldose residue). This sugar residue ($R^1$) can be represented, for example, by $$-[CH(OH)]_n-CH_2OH$$

wherein n is an integral number of 0 to 6.

In the Formula (1), $R^2$ is not particularly limited however is, for example, an amino acid residue or a peptide residue represented by the following Formula (2).

$$-CHR^3-CO-R^4 \quad (2)$$

In Formula (2), $R^3$ represents an amino acid side chain group, $R^4$ represents a hydroxyl group, an amino acid residue or a peptide residue, and can be represented, for example, by Formula (3) below. In Formula (3), n is an integer of 0 or more, $R^3$ represents an amino acid side chain group as in the above, and the amino acid side chain groups may be either the same or different.

$$-(NH-CHR^3-CO)_n-OH \quad (3)$$

As for such FAOD-α, for example, fructosyl amine oxidase disclosed in WO2004/029251 A1, fructosyl amine oxidase disclosed in JP2004-275013 A and JP2004-275063 A, FAOD derived from *penicillium* (JP8-336386 A), and the like can be used. Use of such FAOD allows the measurement of HbA1c with higher accuracy because the FAOD hardly acts on a glycated part other than a valine even when a portion other than the β chain N-terminal valine is glycated.

FAOD may further include a substrate specificity besides the Formula (I). An example of such FAOD includes one that acts on both the glycated α-amino group and the glycated amino acid side chain group (hereinafter, referred to as "FAOD-αS"). Specific examples thereof include FPDX-CE (trade name) manufactured by KIKKOMAN Corporation, FPDX-EE (trade name) manufactured by KIKKOMAN Corporation, FOD (trade name, commercially available) manufactured by Asahi Kasei Corporation, FAOD derived from *gibberella* (JP8-154672 A), FAOD derived from *fusarium* (JP7-289253 A), FAOD derived from *aspergillus* (WO97/20039 A1), etc. In a case of such FAOD, for example, by suitably selecting the type of protease and combining with the protease that specifically cleaves peptide and amino acid of the β chain N-terminal, an action thereof on the other glycated part can be prevented.

Preferably, a FAOD treatment is performed in a buffer solution the same as in the case of the protease treatment. The buffer solution is not particularly limited and the similar one used in the protease treatment can be used. Conditions of the FAOD are not particularly limited. For example, pH of a reaction solution is 6 to 9 and a treatment temperature is, for example, in the range of 10 to 38° C., and preferably in the range of 25 to 37° C. A treatment time also is not particularly limited and is, for example, 0.1 to 60 minutes, and preferably 0.1 to 5 minutes.

A ratio of FAOD to be added in a reaction solution of FAOD is, for example, in the range of 0.01 to 50 KU/L, and preferably in the range of 0.5 to 10 KU/L. With respect to an activity of FAOD "U", an amount generating 1 micromole of hydrogen peroxide per minute by making fructosylvaline as a substrate is defined as 1U.

(Measurement of Redox Reaction)

Next, a measurement of a redox reaction between the glycated part and the FAOD is performed. Examples of this measurement may include, for example, a measurement of a hydrogen peroxide amount generated by the reaction and a measurement of an oxygen amount that is consumed in the reaction. The hydrogen peroxide amount can be measured, for example, with peroxidase (POD) and a substrate that develops a color by oxidation, by developing the color of the substrate by the reaction thereof with hydrogen peroxide, and measuring a level of this color. Further, besides an enzyme method using POD, etc., the hydrogen peroxide amount can be measured by an electrical method.

The above-mentioned substrate that develops the color by oxidation (chromogenic substrate) is not particularly limited and includes N-(carboxymethylaminocarbonyl)-4,4'-bis (dimethylamino) diphenylamine sodium (trade name: DA-64 manufactured by Wako Pure Chemical Industries, Ltd.), 10-

(carboxymethylaminocarbonyl)-3,7-bis(dimethylamino) phenothiazine or its salt (for example, trade name: DA-67 manufactured by Wako Pure Chemical Industries, Ltd.), N,N, N',N',N",N"-hexa(3-sulfopropyl)-4,4',4"-triaminotriphenyl-methanehexaso dium salt (for example, trade name: TPM-PS manufactured by DOJINDO LABORATORIES), N-(carboxymethylaminocarbonyl)-4,4'-bis(dimethylamino) diphenylamine sodium, orthophenylendiamin (OPD), a substrate of a combination of Trinder's reagent and 4-aminoantipyrine, etc. The Trinder's reagent can be, for example, phenols, phenol derivatives, aniline derivatives, naphthols, naphthol derivatives, naphthylamine, naphthylamine derivatives or the like. Besides the 4-aminoantipyrine noted above, it also is possible to use aminoantipyrine derivatives, vanillin diamine sulfonic acid, methylbenzothiazolinone hydrazone (MBTH), sulfonated methyl benzothiazolinone hydrazone (SMBTH), or the like.

A ratio of the chromogenic substrate to be added in the reaction solution is, for example, in the range of 0.001 to 10 mM and preferably in the range of 0.004 to 2 mM.

POD reaction preferably is performed in a buffer solution the same as in the case of the protease treatment and the aforementioned buffer solution may be used. Conditions of a POD treatment are not particularly limited. For example, pH of the reaction solution is 5 to 9, and a treatment temperature is, for example, in the range of 10 to 40° C., preferably in the range of 25 to 37° C. A treatment time also is not particularly limited and is, for example, 0.1 to 5 minutes.

A ratio of the POD to be added in a POD reaction solution is, for example, in the range of 0.01 to 300 KU/L and preferably in the range of 0.5 to 40 KU/L. Further, a ratio of the chromogenic substrate to be added in the reaction solution is, for example, in the range of 0.001 to 10 mM and preferably in the range of 0.004 to 2 mM. With respect to an activity of POD "U", an amount oxidizing 1 micromole of guaiacol per minute is defined as 1U.

In the case of using the chromogenic substrate as described above, for example, the developed color (for example, an absorbance of the reaction solution) may be measured by a spectrophotometer. Since the hydrogen peroxide amount corresponds to the glycation amount of the N-terminal valine of Hb (i.e., HbA1c amount, HbA1c concentration, and glycation concentration), the glycation amount of the N-terminal valine can be calculated from the measured absorbance. In this manner, the HbA1c amount can be measured.

Then, by calculating a ratio (%) between this glycation amount of the N-terminal valine of Hb and a total Hb amount (Hb concentration) in the sample based on the below Formula, the HbA1c % (HbA1c ratio) can be obtained. Incidentally, the Hb amount can be measured by a conventionally known method or by using a commercially available reagent kit.

HbA1c %=(glycation amount of β chain N-terminal valine/Hb amount)×100

The glycation amount of the N-terminal valine can be calculated from the absorbance, by using a standard curve obtained by plotting a relationship between the known glycation amount of the N-terminal valine of Hb and the absorbance. For example, with respect to an Hb reference solution whose N-terminal valine glycation amount is known, the absorbance measurement is performed in the same manner as described above, and a standard curve showing a relationship between the measurement value of this reference solution and the known glycation amount is formed. Then, the absorbance measured as described above is substituted into this standard curve, thereby calculating the glycation amount of the N-terminal valine (HbA1c amount).

As described above, the chromogenic substrate is not particularly limited. For example, a substrate that generates methylene blue by reacting with hydrogen peroxide such as the DA-67 is preferable. Methylene blue generated from such chromogenic substrate has a maximal absorption at a relatively long-wavelength side (about 666 nm). Therefore, for example, even when a whole blood sample contains a component having an absorption in a wavelength region of around 500 nm or lower, fluctuation in absorbance because of them can be avoided and thus a measurement with higher accuracy can be performed. Further, when such a chromogenic substrate is used, it is preferable that the pigment substance described below further is added to the reaction solution in advance of an absorbance measurement. In this manner, the presence of such pigment substance allows methylene blue to be detected at a further high wavelength side (at least 660 nm), although the mechanism is unknown. Therefore, for example, even when a whole blood sample contains a component that indicates its absorption at 660 nm, an effect thereof can be avoided and thus a measurement with higher accuracy can be performed. In this state, a timing of adding the pigment substance is not limited at all as long as the pigment substance is added before the absorbance measurement. For example, the pigment substance may be added before or after the generation of methylene blue or may be added simultaneously with the chromogenic substrate or oxidase.

Examples of the pigment substance include 5-hydroxy-1-(4-sulfophenyl)-4-(4-sulfophenylazo)-3-pyrazolecarboxylic acid or its salt (e.g. trisodium salt), 6-hydroxy-5-(4-sulfophenylazo)-2-naphthalenesulfonic acid or its salt (e.g., disodium salt), 3-hydroxy-4-(4-sulfonaphtylazo)-2,7-naphthalenedisulfonic acid or its salt (e.g., trisodium salt), 7-hydroxy-8-(4-sulfonaphtylazo)-1,3-naphthalenedisulfonic acid or its salt (e.g., trisodium salt) or hydrate (e.g., 11/2 hydrate), etc. Examples of those salts and hydrates include commercial products such as tartrazine, Food Yellow No. 5, Food Red No. 2, Food Red No. 102, etc. Further, examples of the pigment substance include 3',6'-dihydroxy-2',4',5',7'-tetraiodospiro[isobenzofuran-1(3H), 9'-(9H)xanthene]-3-on or its salt (e.g., disodium salt) or hydrate (e.g., monohydrate), 3',6'-dihydroxy-2',4',5',7'-tetrabromo-4,5,6,7,-tetrachlorospiro[isobenzofuran-[(3H), 9'-[9H]xanthene]-3-on or its salt (e.g., disodium salt), 4,5,6,7,-tetrachloro-3',6'-dihydroxy-2',4',5', 7',-tetraiodospiro[isobenzofuran-[(3 H),9'-[9H]xanthene]-3-on or its salt (e.g., disodium salt), etc. Examples of those salts and hydrates include Food Red No. 3, Food Red No. 104, Food Red No. 105, etc. Further, an anthocyanin polymer (e.g., a commercially available cacao pigment (Cacao color from *Theobroma cacao* LINNE), a persimmon pigment (Japanese persimmon color from Diospyros kaki THUNB), etc. A ratio of the pigment substance to be added is not particularly limited however is, for example, 0.1 to 1000 mol, preferably 1 to 500 mol, and more preferably 2 to 100 mol per mol of the chromogenic substrate. Further, a final concentration in the reaction solution is, for example, $10^{-6}$ to 0.1 mol/L, preferably $10^{-5}$ to 0.05 mol/L, and more preferably 0.00005 to 0.03 mol/L.

With respect to a measurement of HbA1c amount and HbA1c %, each treatment process may be performed separately as described above. However, for example, each treatment may simultaneously be performed in combinations as described below. Further, an order of adding protease, FAOD, POD, and the chromogenic substrate is not particularly limited.

1: hemolysis treatment+protease treatment
2: hemolysis treatment+protease treatment+FAOD treatment
3: hemolysis treatment+protease treatment+FAOD treatment+POD treatment
4: protease treatment+FAOD treatment
5: protease treatment+FAOD treatment+POD treatment
6: FAOD treatment+POD treatment The first method of measuring HbA1c may be performed, for example, with a reagent kit as described below. The reagent kit may have any structure as long as the first method of measuring HbA1c of the present invention can be performed. An example of a first reagent includes a reagent containing FAOD and oxidase, an example of a second reagent includes a reagent containing protease and the chromogenic substrate. With respect to such reagent kit, for example, by further adding the second reagent after mixing a hemoglobin-containing sample with the first reagent, all processes of the protease treatment, the FAOD treatment, the chromogenic reaction can be started.

Besides FAOD and oxidase (e.g., POD), the first reagent further may include a buffer agent, the accelerating compound, and the pigment substance. Further, besides the protease and the chromogenic substrate, the second reagent further may include the buffer agent and the pigment substance. A ratio of each component contained in each reagent is not particularly limited. However, it is preferable that each reagent is prepared such that a concentration of each component in the reaction solution falls within the aforementioned range.

Second Method of Measuring HbA1c

A second method of measuring HbA1c of the present invention includes:

(A2') a process of adding a strong electrolyte substance having a positive ion at least one selected from the group consisting of $K^+$, $Na^+$, and $Mg^{2+}$ and a negative ion at least one selected from the group consisting of $Cl^-$, $SO_4^{2-}$, and $NO_3^-$ to whole blood after storage (producing a whole blood sample after storage);

(B) a process of cleaving hemoglobin in a hemoglobin-containing sample by applying a protease treatment to the hemoglobin-containing sample after storage;

(C) a process of treating a glycated part of a hemoglobin fragment obtained by the process (B) with fructosyl amine oxidase; and (D) a process of determining a HbA1c amount by measuring a redox reaction between the glycated part and the fructosyl amine oxidase.

According to the second method of measuring HbA1c, even when a steric structure of Hb is converted to a deoxy form because carbon dioxide is generated due to storage of a hemoglobin-containing material, by adding the strong electrolyte substance, fluctuation in a measurement value of HbA1c because of storage can be prevented. This may be because the steric structure of Hb can be reconverted to an oxy form, for example, by dissociating (removing) carbon dioxide bonded to Hb by the strong electrolyte substance even when the steric structure of Hb is converted to the deoxy form because of carbon dioxide generated due to storage.

The second method of measuring HbA1c is characterized by adding the strong electrolyte substance to the hemoglobin-containing material after storage, and conditions in other processes are not limited at all. By adding the strong electrolyte substance to the hemoglobin-containing material after storage, normally in the process (B), the protease treatment is performed in a presence of the strong electrolyte substance. Further, for example, the processes (B) and (C) may be performed simultaneously in the same reaction solution. The process (D) may be performed at the same time with the process (C) (and process (B)).

Next, the second method of measuring HbA1c of the present invention is explained with an example in which the whole blood is stored as the Hb-containing material. However, the present invention is not limited thereto and may be performed in the same manner with respect to the Hb-containing material such as diluted whole blood, hemolyzed whole blood, blood cell, purified Hb, etc. Further, the second method of measuring HbA1c is not limited except that the Hb-containing sample after storage is produced by the method of producing of the present invention in the process (A2'), for example. The second method of measuring HbA1c may be performed in the same manner as the first method of measuring HbA1c unless otherwise mentioned. Further, the processes (B) to (D) of the second method of measuring HbA1c respectively correspond to the processes (B) to (D) of the first method of measuring HbA1c and they are the same processes unless otherwise mentioned.

(Storage of Whole Blood)

Whole blood is collected from a test body and stored until a measurement of HbA1c. Although storage of the whole blood may not be necessary in the measurement of HbA1c, because an object of the present invention is to prevent fluctuation in a HbA1c value, the present invention preferably is applied in a case where storage of the whole blood is required.

In this embodiment, in contrast to the first method of measuring HbA1c, it is not required to store the whole blood in the presence of the glycolytic inhibitor. Therefore, for example, a type of a blood collecting tube is not limited at all. For example, a blood collecting tube that does not contain the glycolytic inhibitor may be used.

(Hemolysis Treatment)

A whole blood sample after storage is subjected to a hemolysis treatment. Conditions of the hemolysis treatment are, for example, as same as in the first method of measuring HbA1c. The strong electrolyte substance may be added before or after the hemolysis treatment.

(Addition of Strong Electrolyte Substance)

The strong electrolyte substance is added to the hemolyzed whole blood. Thereby, the whole blood sample after storage to be subjected to the measurement of HbA1c can be prepared.

Examples of the strong electrolyte substance include KCl, $K_2SO_4$, $KNO_3$, NaCl, $Na_2SO_4$, $NaNO_3$, $MgCl_2$, $MgSO_4$, and $Mg(NO_3)_2$. Besides those examples, $Ca(NO)_2$ can be used. Among them, KCl, NaCl, $K_2SO_4$, and $MgSO_4$ are preferable. Further, the strong electrolyte substance may be used alone or two or more of them may be used in combination. A combination of two or more of the strong electrolyte substance is not particularly limited. Examples of the combination include a combination of KCl and $MgSO_4$, a combination of NaCl and $MgSO_4$, and a combination of $K_2SO_4$ and $MgSO_4$. In the present invention, a reagent containing the strong electrolyte substance can be used as a treatment reagent for reducing carbon dioxide bonded to Hb in the stored whole blood. This treatment reagent further may include, for example, protease.

A ratio of the strong electrolyte substance to be added relative to the whole blood is, for example, 5 to 3000 mol and preferably 8 to 1000 mol per ml of the whole blood. Further a concentration of the strong electrolyte substance in a reaction solution in the protease treatment which is the next process is, for example, 10 to 3000 mmol/L, preferably 40 to 1000 mmol/L, and particularly preferably 40 to 350 mmol/L. When a concentration of Hb in the reaction solution is 0.005 mM, a ratio of the strong electrolyte substance to be added is, for example 10 to 3000 mmol/L, preferably 40 to 1000 mmol/L, and particularly preferably 40 to 350 mmol/L.

Besides the aforementioned untreated whole blood, for example, in a case where diluted whole blood, hemolyzed whole blood, blood cell, purified Hb, etc. are stored, they can be treated in the same manner by the strong electrolyte substance. A ratio of the strong electrolyte substance to be added is not particularly limited. For example, the ratio can be set in the aforementioned range by converting the diluted whole blood, the hemolyzed whole blood, the blood cell, the purified Hb, etc. into a whole blood amount. The same applies to the other processes.

(Protease Treatment)

The hemolyzed whole blood sample is subjected to the protease treatment in a presence of the strong electrolyte substance.

In the protease treatment, it is preferable that the reaction solution further contains at least one of NaOH and Tris (tris hydroxymethyl aminomethane). By adding those, fluctuation in HbA1c particularly in a case where the whole blood sample is subjected to freeze preservation can efficiently be prevented. The same applies to the first method of measuring HbA1c. A temperature of the freeze preservation is, for example, −15 to −80° C. and is normally at −80° C.

A ratio of NaOH to be added in the reaction solution is, for example, 5 to 3000 mmol/L, preferably 30 to 1000 mmol/L, and particularly preferably 40 to 350 mmol/L. Further, a ratio of Tris to be added is, for example, 5 to 3000 mmol/L, preferably 30 to 1000 mmol/L, and particularly preferably 40 to 350 mmol/L.

After the protease treatment, HbA1c may be calculated by performing a FAOD treatment and a measurement of the redox reaction in the same manner as the first method of measuring HbA1c.

The second method of measuring HbA1c may be performed, for example, with the reagent kit as described below. The reagent kit may have any structure as long as the second method of measuring HbA1c of the present invention can be performed. An example of a first reagent includes a reagent containing FAOD, oxidase, and the strong electrolyte substance and an example of a second reagent includes a reagent containing protease and the chromogenic substrate. With respect to such reagent kit, for example, by further adding the second reagent after mixing the whole blood with the first reagent, all processes of the protease treatment, the FAOD treatment, and the chromogenic reaction can be started.

Besides the FAOD, the oxidase (e.g., POD), and the strong electrolyte substance, the first reagent may further include the aforementioned NaOH, Tris, a buffer agent, the accelerating compound, and the pigment substance. Further, besides the protease and the chromogenic substrate, the second reagent may further include the buffer agent and the pigment substance. A ratio of each component contained in each reagent is not particularly limited. However, it is preferable that each reagent is prepared such that a concentration of each component in the reaction solution falls within the aforementioned range.

Hereinafter, the present invention is explained more specifically with examples. However, the present invention is not limited thereto.

Example 1

Whole blood collected by various types of blood collecting tubes was stored, and thereafter HbA1c % thereof was measured to confirm whether HbA1c % was fluctuated.

Whole blood was collected from healthy subjects using the following blood collecting tubes and the whole blood was stored with the blood collecting tubes being sealed. The blood collecting tubes were left at 4° C. for 15 days, and then Hb and HbA1c of the whole blood were measured.

(Blood Collecting Tube)

H tube: heparin sodium blood collecting tube (manufactured by Terumo)

DK tube: EDTA-K blood collecting tube (manufactured by Terumo)

FH tube: sodium fluoride+heparin sodium blood collecting tube (manufactured by Terumo)

TABLE 1

| (First Reagent) | |
|---|---|
| FPOX-CE | 1.5 KU/L |
| POD | 10 KU/L |
| PIPES | 30 mmol/L(pH 7) |
| n-dodecyl-αβ-D-maltoside | 2.5 g/L |
| $KNO_2$ | 4 mmol/L |
| Tartrazine* | 0.15 g/L |
| (Second Reagent) | |
| Metalloprotease (manufactured by Arkray, Inc.) | 1800 KU/L |
| $CaCl_2$ | 5 mmol/L |
| Tris | 70 mmol/L |
| MES | 30 mmol/L (pH 5.5) |
| Hexadecyltrimethylammonium Chloride | 0.2 g/L |
| Tartrazine | 0.10 g/L |
| DA-67 (manufactured by Wako Pure Chemical Industries, Ltd.) | 0.03 mmol/L |

*5-hydroxyl-1-(4-sulfophenyl)-4-(4-sulfophenylazo)-3-pyrazolecarboxylic acid/trisodium salt (hereinafter, the same applies)

<Method of Measuring HbA1c>

Whole blood that was left for 15 days was diluted with purified water by 26 times. Then, 6.5 μL of purified water was added to 6.5 μL of this diluted solution, thereby preparing a sample. 13 μL of this sample was mixed with 78 μL of the first reagent and incubated at 37° C. for 5 minutes. In this state, with respect to this reaction solution, an absorbance measurement ($B_1$) at a wavelength of 571 nm/751 nm and an absorbance measurement ($A_1$) at a wavelength of 694 nm/751 nm were performed. Next, 19.5 μL of the second reagent was further added to the reaction solution and incubated at 37° C. for 5 minutes. Thereafter, with respect to the reaction solution, an absorbance measurement ($A_2$) at a wavelength of 694 nm/751 nm was performed again. Then, as indicated by the following Formula, a value obtained by multiplying a first absorbance ($A_1$) by a value that corrects capacitance change [(13+78)/(13+78+19.5)] was subtracted from a second absorbance ($A_2$), and thereby the obtained value was defined as an absorbance corresponding to a HbA1c concentration in a whole blood sample (HbA1c absorbance). The first absorbance ($B_1$) at wavelength of 571 nm/751 nm corresponds to a Hb concentration in the sample (Hb absorbance). The measurement was performed using a biochemical autoanalyzer (trade name: JCA-BM8 manufactured by JEOL). Further, as a control, an absorbance measurement was performed in the same manner using whole blood right after collection and purified water instead of the whole blood. This absorbance was substituted into a preliminarily prepared standard curve, thereby obtaining HbA1c %. The standard curve was obtained by performing an absorbance measurement in the same manner using a reference sample whose HbA1c % was known and by plotting a relationship between the absorbance and HbA1c % value. These results are shown in the following Table 2.

$$HbA1c\ absorbance = A_2 - [A_1 \times (13+78)/(13+78+19.5)]$$

TABLE 2

| | Types of Blood Collecting Tubes | A1c (mAbs.) | Hb (mAbs.) | A1c/Hb | HbA1c % |
|---|---|---|---|---|---|
| Right After Blood Collection | Purified Water | 6 | 2 | — | — |
| | H tube | 17 | 144 | 0.077 | 3.04 |
| | DK tube | 16 | 139 | 0.073 | 2.88 |
| | FH tube | 16 | 139 | 0.073 | 2.88 |
| 4 days later | Purified Water | 6 | 2 | — | — |
| | H tube | 17 | 142 | 0.079 | 3.12 |
| | DK tube | 16 | 140 | 0.072 | 2.84 |
| | FH tube | 16 | 137 | 0.074 | 2.92 |
| 7 days later | Purified Water | 7 | 2 | — | — |
| | H tube | 16 | 139 | 0.066 | 2.61 |
| | DK tube | 16 | 134 | 0.067 | 2.65 |
| | FH tube | 17 | 135 | 0.076 | 3.00 |
| 11 days later | Purified Water | 8 | 3 | — | — |
| | H tube | 16 | 143 | 0.057 | 2.25 |
| | DK tube | 16 | 139 | 0.059 | 2.33 |
| | FH tube | 18 | 140 | 0.073 | 2.88 |
| 15 days later | Purified Water | 9 | 2 | — | — |
| | H tube | 17 | 180 | 0.056 | 2.21 |
| | DK tube | 18 | 172 | 0.053 | 2.09 |
| | FH tube | 21 | 166 | 0.073 | 2.88 |

A1c/Hb = [A1c (mAbs.) − purified water (mAbs.)]/[Hb(mAbs.) − purified water (mAbs.)]

As shown in Table 2, with respect to the whole blood collected with the blood collecting tube only containing heparin Na and with the blood collecting tube containing EDTA-K, an absorbance was decreased by being left, and as a result, HbA1c % was decreased. This may be because, while the whole blood was left, oxy form Hb was converted to deoxy form Hb due to carbon dioxide generated from the whole blood and thereby a β chain N-terminal side of Hb hardly was treated with the protease. In contrast, when the blood collecting tube containing sodium fluoride was used, HbA1c % scarcely varied even when the collected whole blood was left for 15 days. In other words, even when the whole blood collected from patients was stored, because of a presence of sodium fluoride, HbA1c % can be measured with higher accuracy without fluctuating HbA1c % of right after collection and that of after storage.

It also was confirmed that HbA1c % did not fluctuate during storage by an HPLC method. Specifically, the whole blood collected by the blood collecting tube containing sodium fluoride was left in the blood collecting tube in the same condition as described above. Then, with respect to this whole blood, a measurement of HbA1c % was performed by the HPLC method. For this measurement, ADAMS-A1c HA-8160 manufactured by Arkray, Inc. was used. The result is shown in the following Table. As shown in the following Table, it was confirmed that HbA1c % did not fluctuate due to storage by the HPLC method.

| | HbA1c % |
|---|---|
| Right After Blood Collection | 5.45 |
| 1 day later | 5.35 |
| 5 days later | 5.61 |
| 7 days later | 5.50 |
| 9 days later | 5.56 |
| 12 days later | 5.51 |

Example 2

Various kinds of additives were added to the stored whole blood, and thereafter HbA1c % thereof was measured to confirm whether HbA1c % was fluctuated.

Whole blood was collected from healthy subjects using the heparin sodium blood collecting tube (H tube) and the whole blood was stored in a refrigerator for 2 weeks. Thereafter, Hb and HbA1c of the whole blood were measured. HbA1c % was measured in the same manner as in Example 1 except that the following first-second reagent was used instead of the first reagent. In the following first-second reagent, KOH was added to 30 mmol of PIPES to adjust the pH thereof to 7, and then water was added thereto, thereby preparing 1 L of PIPES/KOH.

TABLE 3

| (First-Second Reagent) | |
|---|---|
| FPOX-CE | 1.5 KU/L |
| POD | 10 KU/L |
| PIPES/KOH | 30 mmol/L(pH 7) |
| n-dodecyl-αβ-D-maltoside | 2.5 g/L |
| $KNO_2$ | 4 mmol/L |
| Tartrazine | 0.15 g/L |
| Additive | Predetermined Amount |

Further, as an evaluation criteria for a system using additives (No. 1 to 22) shown in the following Table 4, HbA1c % was measured after storage in the same manner as in Example 1 with respect to the whole blood collected by the sodium fluoride+heparin sodium blood collecting tube (FH tube). When the whole blood collected by the FH tube was stored, a decrease in HbA1c % can be prevented sufficiently. This was proved in Example 1. Therefore, in a case where a measurement of HbA1c was performed using a system in which various kinds of additives are used with respect to the whole blood collected by the H tube, when the measurement value thereby obtained and a measurement value of the whole blood collected by the FH tube are close, it can be said that the decrease in HbA1c value can be prevented by the system in which the additives are used. The result thereof is shown in the following Tables 5 and 6.

TABLE 4

| Additive No. | KCl (mM) | NaCl (mM) | $K_2SO_4$ (mM) | $MgSO_4$ (mM) |
|---|---|---|---|---|
| 1 | — | — | — | — |
| 2 | 100 | — | — | — |
| 3 | 120 | — | — | — |
| 4 | — | — | — | 40 |
| 5 | — | — | — | 100 |
| 6 | 40 | — | — | 5 |
| 7 | 80 | — | — | 5 |
| 8 | 120 | — | — | 5 |
| 9 | 40 | — | — | 40 |
| 10 | 80 | — | — | 40 |
| 11 | 120 | — | — | 40 |
| 12 | — | 120 | — | — |
| 13 | — | 40 | — | 5 |
| 14 | — | 80 | — | 5 |
| 15 | — | 120 | — | 5 |
| 16 | — | 40 | — | 40 |
| 17 | — | 80 | — | 40 |
| 18 | — | 120 | — | 40 |
| 19 | — | — | 120 | 5 |
| 20 | — | — | 20 | 40 |
| 21 | — | — | 60 | 40 |
| 22 | — | — | 120 | 40 |

TABLE 5

| Additive No. | Specimen | A1c (mAbs.) | Hb (mAbs.) | A1c/Hb | HbA1c % |
|---|---|---|---|---|---|
| 1 | Purified Water | 25 | 3 | — | — |
| | FH Tube (Criteria) | 34 | 165 | 0.056 | 3.30 |
| | H Tube (Comparative Example) | 32 | 175 | 0.041 | 2.42 |
| 2 | Purified Water | 15 | 3 | — | — |
| | FH Tube (Criteria) | 22 | 119 | 0.060 | 3.54 |
| | H Tube | 22 | 121 | 0.059 | 3.48 |
| 3 | Purified Water | 26 | 3 | — | — |
| | FH Tube (Criteria) | 32 | 166 | 0.037 | 2.18 |
| | H Tube | 32 | 174 | 0.035 | 2.07 |
| 4 | Purified Water | 26 | 3 | — | — |
| | FH Tube (Criteria) | 35 | 166 | 0.055 | 3.25 |
| | H Tube | 35 | 174 | 0.053 | 3.13 |
| 5 | Purified Water | 26 | 3 | — | — |
| | FH Tube (Criteria) | 34 | 166 | 0.049 | 2.89 |
| | H Tube | 35 | 173 | 0.053 | 3.13 |
| 6 | Purified Water | 26 | 3 | — | — |
| | FH Tube (Criteria) | 32 | 164 | 0.037 | 2.18 |
| | H Tube | 32 | 174 | 0.035 | 2.07 |
| 7 | Purified Water | 27 | 3 | — | — |
| | FH Tube (Criteria) | 34 | 167 | 0.043 | 2.54 |
| | H Tube | 34 | 175 | 0.041 | 2.42 |
| 8 | Purified Water | 27 | 3 | — | — |
| | FH Tube (Criteria) | 33 | 166 | 0.037 | 2.18 |
| | H Tube | 34 | 174 | 0.041 | 2.42 |
| 9 | Purified Water | 27 | 3 | — | — |
| | FH Tube (Criteria) | 34 | 167 | 0.043 | 2.54 |
| | H Tube | 34 | 174 | 0.041 | 2.42 |
| 10 | Purified Water | 27 | 3 | — | — |
| | FH Tube (Criteria) | 33 | 166 | 0.037 | 2.18 |
| | H Tube | 33 | 174 | 0.035 | 2.07 |
| 11 | Purified Water | 27 | 3 | — | — |
| | FH Tube (Criteria) | 34 | 166 | 0.037 | 2.18 |
| | H Tube | 34 | 174 | 0.035 | 2.07 |

TABLE 6

| Additive No. | Specimen | A1c (mAbs.) | Hb (mAbs.) | A1c/Hb | HbA1c % |
|---|---|---|---|---|---|
| 12 | Purified Water | 26 | 3 | — | — |
| | FH Tube (Criteria) | 33 | 166 | 0.043 | 2.54 |
| | H Tube | 33 | 174 | 0.041 | 2.42 |
| 13 | Purified Water | 26 | 3 | — | — |
| | FH Tube (Criteria) | 35 | 165 | 0.056 | 3.30 |
| | H Tube | 35 | 174 | 0.053 | 3.13 |
| 14 | Purified Water | 26 | 3 | — | — |
| | FH Tube (Criteria) | 34 | 166 | 0.049 | 2.89 |
| | H Tube | 35 | 174 | 0.053 | 3.13 |
| 15 | Purified Water | 27 | 3 | — | — |
| | FH Tube (Criteria) | 34 | 166 | 0.043 | 2.54 |
| | H Tube | 34 | 173 | 0.041 | 2.42 |
| 16 | Purified Water | 27 | 3 | — | — |
| | FH Tube (Criteria) | 34 | 165 | 0.043 | 2.54 |
| | H Tube | 35 | 173 | 0.047 | 2.77 |
| 17 | Purified Water | 27 | 3 | — | — |
| | FH Tube (Criteria) | 34 | 165 | 0.043 | 2.54 |
| | H Tube | 34 | 173 | 0.041 | 2.42 |
| 18 | Purified Water | 27 | 3 | — | — |
| | FH Tube (Criteria) | 34 | 166 | 0.043 | 2.54 |
| | H Tube | 34 | 173 | 0.041 | 2.42 |
| 19 | Purified Water | 21 | 3 | — | — |
| | FH Tube (Criteria) | 30 | 172 | 0.055 | 3.25 |
| | H Tube | 30 | 168 | 0.055 | 3.25 |
| 20 | Purified Water | 21 | 3 | — | — |
| | FH Tube (Criteria) | 30 | 172 | 0.053 | 3.13 |
| | H Tube | 30 | 168 | 0.055 | 3.25 |
| 21 | Purified Water | 21 | 3 | — | — |
| | FH Tube (Criteria) | 30 | 172 | 0.053 | 3.13 |
| | H Tube | 30 | 168 | 0.054 | 3.19 |
| 22 | Purified Water | 21 | 3 | — | — |
| | FH Tube (Criteria) | 30 | 172 | 0.053 | 3.13 |
| | H Tube | 30 | 167 | 0.055 | 3.25 |

As shown in Tables 4-6, with respect to a system using the additive 1 in which KCl, etc. was not added, HbA1c % of the whole blood collected by the H tube was decreased greatly due to storage compared to that of the whole blood collected by the FH tube indicated in Example 1. In contrast, with respect to systems in which the whole blood collected by the H tube was stored and additives containing KCl, etc. were added at the time of measurement (Additives No. 2 to 22), even with the whole blood after storage, HbA1c % substantially equal to a case in which the whole blood was collected by the FH tube could be obtained, and decrease in HbA1c % could be prevented by the additives.

Example 3

Whole blood collected by a heparin blood collecting tubes was immediately stored at −80° C. (60 days). Then, after the whole blood was thawed at room temperature, HbA1c % thereof was measured to confirm whether HbA1c % was fluctuated. HbA1c % was measured in the same manner as in Example 2 except that the whole blood was subjected to freeze preservation, additives shown in the following Table 7 were used as the additives in the first-second reagent, and PIPES/Tris or PIPES/NaOH instead of PIPES/KOH was used as a buffer solution in the first-second reagent. The result is shown in the following Table 8.

TABLE 7

| Additive No. | KCl (mM) | NaCl (mM) | $K_2SO_4$ (mM) | $MgSO_4$ (mM) | Buffer Solution |
|---|---|---|---|---|---|
| 1 | — | — | — | — | PIPES/Tris 30 mmol/L pH7 |
| 23 | 120 | — | — | 5 | |
| 24 | 40 | — | — | 40 | |
| 25 | 40 | — | — | 100 | |
| 26 | — | — | 120 | 5 | |
| 27 | — | — | 20 | 40 | |
| 28 | — | — | 60 | 40 | |
| 29 | — | — | 120 | 40 | |
| 30 | — | — | — | 40 | PIPES/NaOH 30 mmol/L pH7 |
| 31 | — | 80 | — | 40 | |

TABLE 8

| Additive No. | Specimen | A1c (mAbs.) | Hb (mAbs.) | A1c/Hb | HbA1c % |
|---|---|---|---|---|---|
| 1 | Purified Water | 25 | 3 | — | — |
| | FH Tube (Criteria) | 34 | 165 | 0.056 | 3.30 |
| | H Tube (−80° C.) | 33 | 164 | 0.049 | 2.89 |
| 23 | Purified Water | 21 | 3 | — | — |
| | FH Tube (Criteria) | 33 | 171 | 0.071 | 2.80 |
| | H Tube (−80° C.) | 32 | 160 | 0.070 | 2.77 |
| 24 | Purified Water | 21 | 3 | — | — |
| | FH Tube (Criteria) | 32 | 172 | 0.065 | 2.57 |
| | H Tube (−80° C.) | 32 | 159 | 0.071 | 2.80 |
| 25 | Purified Water | 21 | 3 | — | — |
| | FH Tube (Criteria) | 32 | 170 | 0.066 | 2.61 |
| | H Tube (−80° C.) | 31 | 159 | 0.064 | 2.53 |
| 26 | Purified Water | 21 | 3 | — | — |
| | FH Tube (Criteria) | 34 | 170 | 0.078 | 3.08 |
| | H Tube (−80° C.) | 32 | 160 | 0.070 | 2.77 |
| 27 | Purified Water | 20 | 3 | — | — |
| | FH Tube (Criteria) | 33 | 171 | 0.077 | 3.04 |
| | H Tube (−80° C.) | 32 | 159 | 0.077 | 3.04 |
| 28 | Purified Water | 20 | 3 | — | — |
| | FH Tube (Criteria) | 33 | 172 | 0.077 | 3.04 |
| | H Tube (−80° C.) | 32 | 158 | 0.077 | 3.04 |
| 29 | Purified Water | 20 | 3 | — | — |
| | FH Tube (Criteria) | 33 | 171 | 0.077 | 3.04 |
| | H Tube (−80° C.) | 32 | 159 | 0.077 | 3.04 |

TABLE 8-continued

| Additive No. | Specimen | A1c (mAbs.) | Hb (mAbs.) | A1c/Hb | HbA1c % |
|---|---|---|---|---|---|
| 30 | Purified Water | 20 | 3 | — | — |
| | FH Tube (Criteria) | 33 | 170 | 0.079 | 3.12 |
| | H Tube (−80° C.) | 32 | 158 | 0.077 | 3.04 |
| 31 | Purified Water | 21 | 3 | — | — |
| | FH Tube (Criteria) | 32 | 170 | 0.066 | 2.61 |
| | H Tube (−80° C.) | 31 | 158 | 0.065 | 2.57 |

As shown in Table 8, with respect to a system using the additive 1 in which KCl, etc. was not added, HbA1c % of the whole blood was decreased greatly due to storage at −80° C. compared to that of the whole blood collected by the FH tube indicated in Example 1. In contrast, even when the whole blood was collected by the H tube, with respect to the systems of the additives 23 to 31, HbA1c % substantially equal to that of the whole blood collected by the FH tube could be obtained. Accordingly, decrease in HbA1c % could be prevented.

Example 4

Additives ($K_2SO_4$ and $MgSO_4$) were added to the stored whole blood, and thereafter HbA1c % thereof was measured to confirm whether HbA1c % was fluctuated.

$K_2SO_4$ (60 mmol/L) and $MgSO_4$ (40 mmol/L) were added as the additives to the first-second reagent of Example 3, thereby preparing a first-second reagent. Then, the whole blood was collected from healthy subjects by the heparin sodium blood collecting tube (H tube) and an EDTA-2K blood collecting tube. The whole blood was stored in a refrigerator for a predetermined period (0, 1, 4, 6, and 11 days) in a state in which the blood is left in the collecting tubes. Thereafter, Hb and HbA1c of the whole blood were measured. HbA1c % was measured in the same manner as in Example 1 except that the aforementioned first-second reagent was used instead of the first reagent. In this state, as a control, the first-second reagent in which purified water was added instead of $K_2SO_4$ and $MgSO_4$ was used. The result is shown in the following Table 9.

TABLE 9

| Blood Collecting Tube | | Storage Days | | | | |
|---|---|---|---|---|---|---|
| | | 0 day | 1 day | 4 days | 6 days | 11 days |
| EDTA-2K | Example | 5.28 | 5.28 | 5.27 | 5.33 | 5.23 |
| | Reference | 5.43 | 5.40 | 5.38 | 5.19 | 4.74 |
| Heparin Na | Example | 5.26 | 5.26 | 5.29 | 5.25 | 5.26 |
| | Reference | 5.43 | 5.4 | 5.36 | 5.18 | 4.65 |

Unit: HbA1c %

As shown in Table 9, with respect to the control, the measurement values of the whole blood collected by any blood collecting tube were decreased with time. In contrast, with respect to the example, HbA1c % was not fluctuated by performing a measurement in a presence of $K_2SO_4$ and $MgSO_4$.

INDUSTRIAL APPLICABILITY

As described above, according to the present invention, fluctuation in the measurement value of HbA1c can be prevented even when the whole blood sample was stored, and therefore HbA1c can be measured with accuracy substantially equal to that of the whole blood right after collection. In this manner, since an effect of the measurement value of HbA1c due to storage can be removed, it may be very useful in a case in which the sample is required to be stored, namely when the measurement of HbA1c is performed at a place different from a sampling point.

The invention claimed is:

1. A method of measuring HbA1c, wherein the method comprises:
   (A) collecting a hemoglobin-containing material from a subject and storing the collected hemoglobin-containing material for a period of at least one day;
   (B) reducing carbon dioxide bonded to hemoglobin in the hemoglobin-containing material stored in (A) so as to produce a hemoglobin-containing sample;
   (C) cleaving the hemoglobin in the hemoglobin-containing sample produced in (B) by applying a protease treatment to the hemoglobin-containing sample;
   (D) treating a glycated part of a hemoglobin fragment obtained from cleaving the hemoglobin in the hemoglobin-containing sample in (C) with fructosyl amine oxidase; and
   (E) determining an amount of HbA1c in the hemoglobin-containing sample by measuring a redox reaction between the glycated part and the fructosyl amine oxidase and calculating the amount of HbA1c based on a measurement of the redox reaction.

2. The method of measuring HbA1c according to claim 1, wherein in (B), a strong electrolyte substance having a positive ion and a negative ion is added to the hemoglobin-containing material stored in (A), the positive ion being at least one selected from the group consisting of $K^+$, $Na^+$, and $Mg^{2+}$, and the negative ion being at least one selected from the group consisting of $Cl^-$, $SO_4^{2-}$, and $NO_3^-$, wherein in (C), the protease treatment is performed in the presence of the strong electrolyte substance.

3. The method of measuring HbA1c according to claim 2, wherein in (C), the protease treatment is conducted in a reaction solution, and a concentration of the strong electrolyte substance in the reaction solution is 10 to 3000 mmol/L.

4. The method of measuring HbA1c according to claim 2, wherein the strong electrolyte substance is at least one selected from the group consisting of KCl, $K_2SO_4$, $KNO_3$, NaCl, $Na_2SO_4$, $NaNO_3$, $MgCl_2$, $MgSO_4$, and $Mg(NO_3)_2$.

5. The method of measuring HbA1c according to claim 1, wherein in (E),
   a HbA1c ratio is calculated from the total amount of the hemoglobin in the hemoglobin-containing sample and the amount of HbA1c in the hemoglobin-containing sample.

6. The method of measuring HbA1c according to claim 1, wherein the hemoglobin-containing sample is a whole blood sample or a blood cell sample.

7. A method of measuring HbA1c, wherein the method comprises:
   (A) collecting a hemoglobin-containing material from a subject and storing the collected hemoglobin-containing material for a period of at least one day in a state in which carbon dioxide generation is inhibited so as produce a hemoglobin-containing sample;
   (B) cleaving hemoglobin in the hemoglobin-containing sample produced in (A) by applying a protease treatment to the hemoglobin-containing sample;
   (C) treating a glycated part of a hemoglobin fragment obtained from cleaving the hemoglobin in the hemoglobin-containing sample in (B) with fructosyl amine oxidase; and
   (D) determining an amount of HbA1c in the hemoglobin-containing sample by measuring a redox reaction between the glycated part and the fructosyl amine oxidase and calculating the amount of HbA1c based on a measurement of the redox reaction.

8. The method of measuring HbA1c according to claim 7, wherein in (A), the hemoglobin-containing material is stored in the presence of a glycolytic inhibitor, and in (B), the protease treatment is conducted in a reaction solution, and a concentration of the glycolytic inhibitor in the reaction solution is 0.01 to 10 mol/L.

9. The method of measuring HbA1c according to claim 7, wherein in (D), a HbA1c ratio is calculated from the total amount of the hemoglobin in the hemoglobin-containing sample and the amount of HbA1c in the hemoglobin-containing sample.

10. The method of measuring HbA1c according to claim 7, wherein the hemoglobin-containing sample is a whole blood sample or a blood cell sample.

11. The method of measuring HbA1c according to claim 7, wherein in (A), the hemoglobin-containing material is stored in the presence of a glycolytic inhibitor.

12. The method of measuring HbA1c according to claim 11, wherein the glycolytic inhibitor is at least one selected from the group consisting of sodium fluoride and potassium fluoride.

* * * * *